United States Patent [19]

Kawahara et al.

[11] Patent Number: 4,647,600
[45] Date of Patent: Mar. 3, 1987

[54] DENTAL CEMENT COMPOSITIONS

[75] Inventors: Haruyuki Kawahara, No. 28, tokocho 1-chome, Moriguchi-shi, Osaka-fu; Shoji Takeda, Ibaraki; Hiroshi Oshima, Sakai; Kentaro Tomioka, Chofu; Shoji Akahane, Higashikurume; Eiichi Yoshii; Kazuo Hirota, both of Tokyo, all of Japan

[73] Assignees: G-C Dental Industrial Corp., Tokyo; Haruyuki Kawahara, Moriguchi, both of Japan

[21] Appl. No.: 828,704

[22] Filed: Feb. 12, 1986

[30] Foreign Application Priority Data

Apr. 5, 1985 [JP] Japan .................................. 59-71064

[51] Int. Cl.[4] ............................................. A61K 5/01
[52] U.S. Cl. ...................................... 523/116; 106/35; 433/228.1; 523/117
[58] Field of Search ................... 106/35; 523/116, 117; 433/228.1

[56] References Cited

U.S. PATENT DOCUMENTS 4,542,167  9/1985  Aoki ..................................... 523/116
4,591,384  5/1986  Akahane et al. ................. 433/228.1

Primary Examiner—Lorenzo B. Hayes
Attorney, Agent, or Firm—Oblon, Fisher, Spivak, McClelland & Maier

[57] ABSTRACT

A dental cement composition consisting of a composition A and a composition B, said composition A comprising at least two powders, (a) 100 parts by weight of a powder containing more than 20% by weight to 70% by weight of calcium oxide and 30% by weight to less than 80% by weight of aluminium oxide and treated on the surface with 0.01 to 5% by weight of at least one selected from the group consisting organic acids and/or inorganic acids, and (b) 2 to 70 parts by weight of a calcium hydroxide powder, and said composition B comprising of an aqueous solution containing 0.01 to 70% by weight of a water-soluble high-molecular substance.

5 Claims, No Drawings

DENTAL CEMENT COMPOSITIONS

FIELD OF THE INVENTION

The present invention relates generally to a dental cement composition and, more particularly, to a dental cement composition best-suited for pulp capping, lining, base and root canal filling. More specifically, the invention is concerned with a dental cement composition consisting of a composition A and a composition B, said composition A comprising at least two powders, (a) 100 parts by weight of a powder containing more than 20% by weight to 70% by weight of calcium oxide and 30% by weight to less than 80% by weight of aluminium oxide and treated on the surface with 0.01 to 5% by weight of at least one selected from the group consisting organic acids and/or inorganic acids, and (b) 2 to 70 parts by weight of a calcium hydroxide powder, and said composition B comprising an aqueous solution containing 0.01 to 70% by weight of a water-soluble high-molecular substance.

BACKGROUND OF THE INVENTION

Dental cements are materials used currently in a wider range of dental fields. For instance, they are used as setting for prosthetic appliances and orthodontic appliances, filling for restoration of caries cavity, lining, base, pulp capping, build up, root canal filling, etc. Of the dental cements, zinc phosphate cement, polycarboxylate cement, glass ionomer cement, etc. have relatively excellent physical properties. However, these cements set because of the reaction between acid and bases. Since acids are used in these system, they cannot be used in the vicinity of the alive dental pulp due to the irritating action of the acids. At present, zinc oxide eugenol cement, calcium hydroxide cement, etc. are used as the pulp capping material at regions adjacent to the dental pulp. In particular, the calcium hydroxide cement is used as the direct pulp capping material. Since these cements are expected to show a pharmaceutial effect, they can be used as the pulp capping material without anxiety to some degrees. However, there is a problem, since they possess physical properties such as low crushing strength and high solubility, which appear to be insufficient for the base material. Where the calcium hydroxide cement is used as the pulp capping or the lining material in, for instance, a very deep cavity, it is required to prepare the so-called "cement base" with glass ionomer cement, zinc phosphate cement and ploycarboxylate cement, each having a relatively high crushing strength, due to the low strength thereof, thus resulting in complicated manipulation. Typical calcium hydroxide cement is prepared by cross-linking of calcium hydroxide with salicylic acid ester. Although this product has a low strength, it shows a certain hardening property. However, this product takes on the paste form showing so strong a hydrohobic property that it is lacking in the affinity with respect to teeth. For that reason, there is also a problem in connection with the interface thereof with respect to teeth.

SUMMARY OF THE INVENTION

As a result of intensive and extensive studies made of the prior art pulp capping cement presenting these problems, it has unexpectedly been found that such problems are resolved by the dental cement composition consisting of a composition A and a composition B, said composition A comprising of at least two powders (a) 100 parts by weight of a powder containing more than 20% by weight to 70% by weight of calcium oxide and 30% by weight to less than 80% by weight of aluminium oxide and treated on the surface with 0.01 to 5% by weight of at least one selected from the group consisting of organic acids and/or inorganic acids, and (b) 2 to 70 parts by weight of a calcium hydroxide powder, and said composition B comprising an aqueous solution containing 0.01 to 70% by weight of a water-soluble high-molecular weight substance.

It is understood that the present invention includes a dental cement composition further containing an X-ray contrast medium. It is also understood that to coat a "powder containing more than 20% by weight to 70% by weight of calcium oxide and 30% by weight to less than 80% by weight of aluminium oxide and treated on the surface with at least one selected from the group consisting of organic acids and/or inorganic acids in an amount of 0.01 to 5 parts by weight per 100 parts by weight of said powder" with a water-soluble high-molecular weight substance makes great contributions to improvements in manipulation properties and preservability of the powder.

In other words, the composition of the present invention shows a much increased crushing strength and a reduced solubility, as compared with the existed calcium hydroxide cement. Due to its particularly high crushing strength, the composition of the present invention allows pulp capping, lining and base to be applied with the same material, and makes manipulation so easy that a period of the time required for clinical treatment is curtailed. A mixed sludge obtained from the composition of the present invention has also an appropriate flowability, and excels in the manipulation property. Furthermore, the hydrophilic property of the invented composition gives rise to another advantage that it adheres closely to teeth due to its very excellent affinity thereto. At the same time, the composition of the present invention offers a further advantage that it shows very good preservability in spite of the fact that the powder is basic.

The "powder containing more than 20% by weight to 70% by weight of calcium oxide and 30% by weight to less than 80% by weight of aluminium oxide" refers to a powder containing calcium aluminate, which can be easily prepared from the starting materials containing calcium and aluminium in the ordinary process. For instance, that powder may be obtained by allowing a calcium-containing substance such as calcium carbonate, hydroxide or oxide to react with an aluminium-containing substance such as aluminium hydroxide, carbonate or oxide at high temperatures, and sintering or melting the reaction product, followed by cooling and pulverization. Sintering or melting may be carried out in the known ordinary process. Suitable amounts of auxiliary aids may then be used. Depending upon the conditions applied, the calcium and aluminium contained in the aforesaid powder form, in addition to CaO and $Al_2O_3$, compounds such as $3CaO \cdot Al_2O_3$, $12CaO \cdot 7Al_2O_3$, $CaO \cdot Al_2O_3$, $CaO \cdot 2Al_2O_3$, $CaO \cdot 6Al_2O_3$, etc. It is to be noted that the addition of suitable amounts of other oxides, fluorides, chlorides, sulfates, phosphates, carbonates and the like may be permitted without any difficulty. These substances serve as sintering aids or fluxes, which make a great contribution to curtailment of the production time. For instance, the substance to be added may include oxides such as, e.g., silicon dioxide, strontium oxide, magnesium oxide and ferric oxide as well as fluorides, chlorides, sulfates, phosphates and the like of calcium, aluminium, strontium, sodium, potassium and the like. Any limitation is not imposed upon the powder according to the present invention, as long as it contains more than 20% by weight to 70% by weight of calcium oxide and 30% by weight to less than 80% by weight of aluminium oxide. It is preferred that the calcium oxide content of said powder is more than 20% by weight to 70% by weight. A more preferable range is 25 to 50% by weight. When the amount of calcium oxide is no higher than 20%, the hardening reaction proceeds too slowly. When that amount exceeds 70%, on the other hand, the hardening of cement sludge is too rapid to shorten a time period allowed for manipulation to an extreme extent and, at the same time, to lower the strength thereof. The proportion of aluminium oxide in said powder is preferably in a range of 30% by weight to less than 80% by weight based on the total weight thereof, but particular preference is given to a range of 50% by weight to 75% by weight. When the amount of aluminium oxide is no higher than 30%, there is a drop of the strength of the hardened cement product. When that amount exceeds 80% by weight, on the other hand, the hardening reaction of mixed cement sludge becomes too slow and unpractical. Since the powder sintered at such a high temperature is easily affected by atmospheric moisture and carbon dioxide due to the strong basicity, there is a problem on the preservation of that powder over a prolonged period.

According to the present invention, however, it has been found that a problem of delays in the hardening period with time can be resolved by permitting the calcium aluminate powder to exist along with at least one selected from organic acids and/or inorganic acids, whereby that powder is treated on the surface therewith, thus introducing improvements into preservability. It has further been found that such treatment of the calcium aluminate powder with said acidic substances increases the flowability of cement during mixing, thus making mixing easy and introducing improvements into the manipulation properties such as an extension of a time period allowed for manipulation. Better results may be obtained, if the calcium aluminate powder is only mixed with the acidic substances. However, more preferred results are attained, if the surface of the calcium aluminate powder is allowed to react with the organic acids and/or inorganic acids to form organic and/or inorganic acid salts. The "organic and inorganic acids" used in the present invention refer to substances showing acidity, and any acidic substance may produce a certain effect. Preferable acids include organic acids such as, e.g., stearic, isostearic, 2-hydroxystearic, dimer, salycylic, acetylsalycylic, tartaric, citric, amino (glycine, proline, alanine, aspartic, lysine, etc.) glutaric, adipic, pimelic, sebacic, suberic, decandicarboxylic, caproic, capric, myristic, undecanoic, pelargonic, cyclohexane carboxylic, lauric, palmitic or like acids, and inorganic acids such as phophoric, pyrophosphoric, hydrochloric of like acids. The present invention may also include salts showing acidity. For instance, mono- or di-basic phosphates are also acidic substances, and are thus embraced in the present invention. Of these acidic substance, particular preference is given to phosphoric acid, monobasic phosphates, pyrophosphoric acid, salycylic acid, various amino acids, myristic acid, isostearic acid and the like. These acidic substance may only be mixed with the powder containing calcium aluminate in a mortar. Alternatively, they may be dissolved or suspended in water or organic solvents such as, e.g. an alcohol, benzene, ether or ketone for the surface treatment of the powder containing calcium aluminate. It is then required that the solvent be evaporated off, and the powder be dried. As already mentioned, it is preferred that some reaction occur between these acidic substance and the surface of the "powder containing more than 20% by weight to 70% by weight of calcium oxide and 30% by weight to less than 80% by weight of aluminium oxide". In this case, however, no problem arises, even when other substances contained in the composition A, viz., calcium hydroxide and an X-ray constrast medium, are treated, at the same time, with the acidic substances. Preferably, the amount of at least one selected from the organic and/or inorganic acids used in the present invention is in a range of 0.01 to 5% by weight per 100 parts by weight of the "powder containing more than 20% by weight to 70% by weight of calcium oxide and 30% by weight to less than 80% by weight of aluminium oxide. In an amount of less than 0.01% by weight, no improvements are introduced into the manipulation properties and preservability while, an amount exceeding 5% by weight, a time period required for hardening is so long that there is a drop of physical properties.

No critical limitation is imposed upon the size of the calcium hydroxide used. Usually, however, that powder should preferably pass through a 80-mesh sieve, more preferably a 120-mesh sieve. Calcium hydroxide has a pharmaceutical effect, and is said to promote the growth of secondary dentin. When it is used with the pulp capping material in the present invention, similar effects are expected. The incorporation of calcium hydroxide also results in improvements in the crushing strength of the hardened cement mass. It is preferred that the amount of calcium hydroxide contained in the composition A is 2 to 70 parts by weight per 100 parts by weight of the "powder containing more than 20% by weight to 70% by weight of calcium oxide and 30% by weight to less than 80% by weight of aluminium oxide". In an amount of less than 2 parts by weight, the calcium oxide does not produce its own effect, whereas in an amount exceeding 70 parts by weight, there is a delay in the initial setting time with the resulting drop of crushing strength.

The X-ray constrast media used in the present invention is not critically limited, and refer to substances of X-ray contrasting ability. However, since the larger the atomic number, the higher the degree of the X-ray absorption, use is usually made of a substance having a relatively large atomic number and of reduced toxicity. For instance, use may be made of metal powders, alloy powders, oxides such as yttrium and zinc oxides, salts such as barium sulfate, calcium tungstate and bismuth oxycarbonate, iodoform, etc. Usually, these X-ray contrast media may be contained in the composition A for use, since they are often insoluble in water. In some cases, however, they may be incorporated into the composition B. In other words, the X-ray contrast media, whether water-soluble or -insoluble, may be suspended in the composition B for use. In some cases, the X-ray contrast media may be mixed, sintered and melted with "a powder containing more than 20% by weight to 70% by weight of calcium oxide and 30% by weight to less than 80% by weight of aluminium oxide" in the composition A, when said "powder" is produced by sintering or melting. It is then noted that the contrasting properties are afforded to "a powder containing more than 20% by weight to 70% by weight of calcium oxide and 30% by weight to less than 80% by weight of aluminium oxide" per se.

The compositions of the present invention, free from any X-ray contrast medium, are also usable in view of the physical properties. Rather, the physical properties of the hardened cement are by no means reduced in the presence of X-ray contrast media as compared with in the absence thereof. However, when dentists use the compositions of the present invention for the actually clinical purpose, i.e. for pulp capping, lining or root canal filling, the provision of the contrasting properties to the material helps diagnosis after treatment, and is one of the requirements that said material should have. Preferably, the X-ray constrast media are present in the compositions of the present invention in an amount of 10 to 50% by weight relative to the overall weight thereof. In an amount of less than 10%, there is a reduced or limited contrasting effect, whereas in an amount exceeding 50%, there is a drop of physical properties. Usually, a range of 10 to 40% by weight is preferred. It is to be noted that the compositions of the present invention can also be applied as the root canal filling material due to their good affinity to living bodies; however, they may contain 50% or more of the contrast medium owing to no need of having crushing strength.

In the present invention, to coat the "100 parts by weight of powder containing more than 20% by weight to 70% by weight of calcium oxide and 30% by weight to no less than 80% by weight of aluminium oxide and treated on the surface with 0.01 to 5% by weight of at least one selected from organic acids and/or inorganic acids" contained in the composition A with a water-soluble high-molecular substance means that the "powder containing more than 20% by weight to 70% by weight of calcium oxide and 30% by weight to less than 80% by weight of aluminium oxide" treated on the surface with the acidic substance is further coated with the water-soluble high-molecular substance. Coating or that powder with the water-soluble high-molecular substance introduces improvements into the manipulation properties during mixing. In other words, a time period allowed for manipulation during mixing is made appropriate without preventing hardening or solidification. There is another advantage that the preservability of that powder is further improved. It is to be understood that, when that powder contained in the composition A is coated with the water-soluble high-molecular substance, simultaneous or individual coating of other substances contained therein (viz., calcium hydroxide, acidic substances, and X-ray contrast medium) with such a substance offers no problem. Such water-soluble high-molecular substances may effectively include polyacrylic acid, sodium polyacrylate, polyethylene imine, polyvinyl alcohol, polyethylene glycol, polyethylene oxide, polyvinyl pyrrolidone, carboxymethyl cellulose, methyl cellulose, hydroxyethyl cellulose, hydroxypropyl cellulose, cellulose acetate phthalate, sodium (or potassium) alginate, gum arabic, etc. Of these, preference is given to polyvinyl pyrrolidone, sodium polyacrylate and hydroxypropyl cellulose. These water-soluble high-molecular substances may be deposited onto the surface of the powder in the conventional process. For instance, after mixing in a ball mill, such substances may mechanochemically be deposited onto the surface of the powder. Alternatively, such a substance may be dissolved or suspended in a solvent such as an alcohol, acetone or water, and the resulting solution is mixed with the pulverized body, followed by removal of the solvent by means of drying, etc. In this case, at least one selected from the aforesaid organic acids and/or inorganic acids may be simultaneously be dissolved or suspended in the same solvent so as to simultaneously treat the surface of the "powder containing more than 20% by weight to 70% by weight of calcium oxide and 30% by weight to less than 80% by weight of aluminium oxide" with no difficulty. The water-soluble high-molecular substance used for coating may have a molecular weight of 1,000 to 1,000,000; however, a preferred molecular weight is in a range of 1,000 to 100,000. Too large a molecular weight gives rise to a disadvantage that the powder cannot uniformly be coated. Too low a molecular weight causes another disadvantage that, unless a large amount of coating is applied, any prominent effect is not brought about, so that the physical properties such as crushing strength deteriorate. Sufficiently, the proportion of the water-soluble high-molecular substance used may usually be no higher than 5% by weight based on the total weight of the pulverized body to be coated, but preference is given to a range of 0.05 to 2% by weight.

The composition A in the composition of the present invention has hydraulic properties, and forms a hardened mass upon mixed just only with water. Thus, it is possible to satisfactorily use the composition of the present invention only by mixing with water. It has unexpectedly been found, however, that the strength of the hardened mass is enhanced by the incorporation of the water-soluble high-molecular substance into the composition B. In addition, a time period allowed for manipulation can be extended without any delay in the initial setting time. It is preferred that the composition B has a certain viscosity, since mixing is then made easy.

As is the case with the water-soluble high-molecular substance for coating the composition A, various water-soluble high-molecular substances may be used for the composition B. Among others, polyvinyl pyrrolidone, polyethylene oxide, sodium polyacrylate and sodium polymethacrylate are particularly preferred. The molecular weight of the water-soluble high-molecular substance used is in a range of, preferably 1,000 to 1,000,000, more preferably 1,000 to 100,000. Too large a molecular weight inhibits the hydration and hardening reactions between an aqueous solution the water-soluble high-molecular substance and the cement powder, makes the initial hardening properties unpreferred so that hardening become slow, and incurs a substantial drop of strength. A molecular weight of less than 1000 makes no contribution to any improvements in crushing strength. The proportion of the water-soluble high-molecular weight substance contained in the composition B may properly be selected from the range of 0.01 to 70% by weight depending upon the molecular weight thereof. The viscosity of the composition B is preferably in a range of 5 to 5,000 cP. However, a more preferable range of viscosity is 10 to 2,000 cP.

No special limitation is placed upon the powder/liquid ratio of the compositions A/B. Although it may be selected depending upon the clinical purpose, the composition A may usually be used in an amount of 1.5 to 5.0 grams per 1 gram of the composition B.

In the following, the present invention will more specifically explained with the non-restrictive examples.

EXAMPLE 1

Two hundreds (200) grams of aluminium hydroxide and 100 grams of calcium carbonate were well blended together in a porcelain mortar. The resulting blended powders were charged in a platinum crucible, and pre-sintered at 1300° C. for 5 hours in an electrical furnace. After the sintered body was cooled off in the air, it was pulverized for 2 hours in a ball mill. Thereafter, the thus pulverized body was sintered at 1350° C. for 3 hours in a platinum crucible. After sintering, the sintered body was pulverized for 2 hours in a ball mill, and allowed to pass through a 150-mesh sieve to obtain powders to be used as calcium aluminate powders. Three (3) grams by weight of primary aluminium phosphate powders were added to 100 grams of the thus obtained powders, and they were well blended together in a mortar. The resulting mixture was sintered at 700° C. for 2 hours. After gradual sintering, 20 grams of calcium hydroxide were well blended together with 100 grams of the thus obtained powders in a ball mill to prepare a composition A.

On the other hand, a composition B was prepared by dissolving 10 grams of sodium polyacrylate (M.W.: 15,000) in 90 grams of pure water.

The thus prepared compositions A and B were mixed together in a proportion of A to B of 2.0 grams to 1.0 gram. For mixing, about one half of the powder of the composition A was mixed with the composition B for 15 seconds, and the remaining portion of composition A was further added and mixed to it. Thus, a mixing time amounted to 30 seconds in all. The resulting product was measured on the initial setting time and crushing strength according to JIS Standard T 6602 for dental zinc phosphate cement. The results were 4 minutes 00 second and 750±20 kg/cm², respectively, which suggested that the product of this example was the best pulp capping and lining cement ever.

EXAMPLE 2

In this example, the composition A of Example 1 was used without any modification, and a 5% aqueous solution of polyvinyl pyrrolidone (M.W.: 50,000) was employed as the composition B.

The compositions A and B were mixed in an A to B proportion of 2.0 grams to 1.0 gram. The resulting product was measured on the physical properties in a process similar to that of Example 1. The results were that the initial setting time was 4 minutes 15 seconds, and the crushing strength was 650±40 kg/cm². These values suggested that the product of this example was the best pulp capping, lining and base cement ever.

EXAMPLES 3 & 4

The compositions B of Examples 1 and 2 were used without any modification, but the composition A was further treated on the surface with polyvinyl pyrrolidone (M.W.: 40,000). More exactly, 16 grams of a 5% methanol solution of polyvinyl pyrrolidone (M.W.: 40,000) were added to and well mixed with 100 grams of each of the composition A of Examples 1 and 2, and the resulting mixture was thereafter dried at 120° C. for 2 hours (Example 1→3, Example 2→4). The thus prepared compositions A and B were mixed together in an A to B proportion of 2.0 grams to 1.0 gram to measure the physical properties of the resulting cements. The results were that the initial setting time was 4 minutes 15 seconds (Example 3) and 4 minutes 30 seconds (Example 4), and the crushing strength was 720±30 kg/cm² (Example 3) and 640±30 kg/cm² (Example 4). These values suggested that the products of these examples were the best pulp capping, lining and base cements ever.

EXAMPLE 5

Two hundreds (200) grams of aluminium hydroxide and 80 grams of calcium carbonate were well blended together in a mortar, and the resulting mixture was placed in a platinum crucible, followed by sintering at 1400° C. for 2 hours in an electrical furnace. After sintering, the sintered body was cooled off in the air. The thus cooled body was well pulverized in a porcelain mortar, and allowed to pass through a 150-mesh sieve to obtain powders to be used as calcium aluminate powders. One (1.0) gram of primary ammonium phosphate was milled with 100 grams of those powders for 1 hour, followed by heating at 200° C. for 2 hours. After heating, 20 grams of barium sulfate and 5 grams of calcium hydroxide were well blended with 75 grams of the cooled powders in a mortar to prepare a composition A.

A composition B was prepared by dissolving 10 grams of sodium polyacrylate (M.W.: 20,000) in 90 grams of pure water.

The thus prepared compositions A and B were mixed together in an A to B proportion of 2.5 grams to 1.0 gram. According to the procedures of Example 1, the initial setting time and crushing strength of the resulting product were measured. The results were that the initial setting time was 4 minutes 15 seconds, and the crushing strength was 670±30 kg/cm², which suggested that the product of this example was the best pulp capping, lining and base cement ever.

EXAMPLE 6

One hundred (100) grams of aluminium oxide, 100 grams of calcium carbonate and 2 grams of calcium fluoride were well blended together in a porcelain mortar. The resulting mixture was placed in a platinum crucible for sintering at 1400° C. for 10 hours in an electrical furnace. After sintering, the sintered body was cooled off in the air, pulverized in a mortar, and allowed to pass through a 150-mesh sieve to obtain powders to be used as calcium alumnate powders. Twenty five (25) grams of barium sulfate and 10 grams of calcium hydroxide were well blended with 65 grams of those powders.

On the other hand, 5 grams of hydroxypropyl cellulose (M.W.: 40,000) and 1 gram of proline were dissolved in 94 grams of ethanol. Then, 15 grams of the thus obtained ethanol solution were gradually added dropwise to 100 grams of the aforesaid powders, while the latter was fully mixed. Thereafter, the powders wetted with the alcohol were spread over an evaporating dish, and dried at 110° C. for 2 hours in a steam drier to evaporate off the ethanol completely. The dried powdery mixture was used as a composition A.

On the other hand, a composition B was prepared by dissolving 10 grams of sodium polycarylate (M.W.: 7,000) and 2 grams of sodium methacrylate (M.W.: 40,000) in 88 grams of water.

The thus obtained compositions A and B were mixed together in an A to B proportion of 3.0 grams to 1.0 gram. According to the procedure of Example 1, the initial setting time and crushing strength of the obtained product were measured. The results were that the initial setting time was 3 minutes 45 seconds, and the crushing strength was 680±40 kg/cm².

EXAMPLE 7

Two hundreds (200) grams of aluminium hydroxide and 160 grams of calcium carbonate were well blended together in a porcelain mortar, and the resulting mixture was charged in a platinum crucible, which was in turn in an electrical furnace for sintering at 1400° C. for 10 hours. After sintering, the sintered body was cooled off in the air, pulverized in a mortar, and allowed to pass through a 150-mesh sieve to obtain powders to be used as calcium aluminate powders. On the other hand, 5 grams of salycilic acid were dissolved in 95 grams of methanol. Eighteen (18) grams of the obtained methanol solution were slowly added dropwise to 100 grams of the calcium aluminate powders, while the latter was amply mixed. The powders wetted with the alcohol were spread over an evaporating dish, and dried at 110° C. for 2 hours in a steam drier to evaporate off the methanol completely. Forty (40) grams of barium sulfate and 10 grams of calcium hydroxide were well blended with 50 grams of those powders to prepare a composition A.

On the other hand, the composition B used was similar to that used in Example 1.

According to Example 1, the compositions A and B were mixed together in an A to B proportion of 2.4 grams to 1.0 gram. By measurement, the initial setting time and crushing strength of the resulting product were found to be 4 minutes 30 seconds and 590±30 kg/cm², respectively.

EXAMPLE 8

Eighteen (18) grams of a 5% acetone solution of polyvinyl pyrrolidone (M.W.: 50,000) were slowly added dropwise to 100 grams of the composition A as used in Example 5, while the latter was amply mixed. The wetted powders were dried at 110° C. for 2 hours in a steam drier to evaporate off the acetone completely to obtain dried powders to be used a composition A.

On the other hand, a composition B was prepared according to the procedure of Example 5.

The compositions A and B were mixed together in an A to B proportion of 2.6 grams to 1.0 gram. By measurement, the initial setting time and crushing strength of the resulting cement were found to be 4 minutes 30 seconds and 660±30 kg/cm², respectively.

EXAMPLE 9

Under well agitation, 20 grams of an acetone solution of 5% polyvinyl pyrrolidone (M.W.: 50,000) slowly added dropwise to 100 grams of powders in a mortar, said powders being calcium aluminate powders treated with an alcohol solution of salycylic acid as used in Example 7, followed by drying. Thereafter, those powders were dried at 110° C. for 2 hours in a steam drier. Then, 45 grams of barium sulfate and 10 grams of calcium hydroxide were well blended with 55 grams of the thus treated powders to obtain a composition A.

The composition B used was similar to that used in Example 5.

The thus obtained compositions A and B were mixed together in an A to B proportion of 2.6 grams to 1.0 gram. According to the procedure of Example 1, the initial setting time and crushing strength of the product were measured. The results were that the initial setting time and crushing strength were 4 minutes 30 seconds and 660±30 kg/cm².

Comparison Example 1

The paste type calcium hydroxide cement (manufactured by C Co. Ltd.) which has been widely used for the pulp capping purpose, was measured on the physical properties according to the procedure of Example 1. It is to be understood that 1.0 gram of a catalyst was mixed with 1.17 grams of the paste. The initial setting time was 3 minutes 30 seconds, and the crushing strength ws 152±7 kg/cm².

Comparison Example 2

The cement powder not coated on the surface with salycilic acid was used in place of the cement powder coated on the surface with salycilic acid in Example 3 and other procedures were the same as in Example 3 to prepare a sample. The compositions A of Example 7, Example 3 and Comparison Example 2 were exposed to air to measure the initial setting time thereof after the lapse of two weeks. The results are:

|  | A/B | Initial setting time | Initial setting time after two weeks |
| --- | --- | --- | --- |
| Ex. 7 | 2.4 g/1.0 g | 4 min. 30 sec. | 4 min. 45 sec. |
| Ex. 9 | 2.6 g/1.0 g | 4 min. 30 sec. | 4 min. 30 sec. |
| C. Ex. 2 | 2.4 g/1.0 g | 4 min. 0 sec. | 6 min. 30 sec. |

From the results given, it is evident that the compositions of the present invention do not vary in the initial setting time, but the composition of Comparison Example 2 was delayed 2 minutes 30 seconds.

From the foregoing results, it is clearly understood that Examples 1 to 9 provide the pulp capping, lining and base cements which are greatly improved over Comparison Examples 1 and 2.

We claim:

1. A dental cement composition consisting of a composition A and a composition B,
    said composition A comprising at least two powders,
    (a) 100 parts by weight of a powder containing more than 20% by weight to 70% by weight of calcium oxide and 30% by weight to less than 80% by weight of aluminium oxide and treated on the surface with 0.01 to 5% by weight of at least one selected from the group consisting organic acids and/or inorganic acids, and (b) 2 to 70 parts by weight of a calcium hydroxide powder, and
    said composition B comprising of an aqueous solution containing 0.01 to 70% by weight of a water-soluble high-molecular substance.

2. A dental cement composition as recited in claim 1, in which said compositions A and/or B contain an X-ray contrast medium.

3. A dental cement composition as recited in claim 1 or 2, in which said powder containing more than 20% by weight to 70% by weight of calcium oxide and 30% by weight to less than 80% by weight of aluminium oxide and treated on the surface with 0.01 to 5% by weight of at least one selected from the group consisting of organic acids and/or inorganic acids is coated with a water-soluble high-molecular substance.

4. A dental cement composition as recited in claim 1, 2 or 3, in which the viscosity of an aqueous solution of the water-soluble high-molecular substance contained in said composition B is 5 to 5,000 cP.

5. A dental cement composition as recited in any one of claims 1 to 4, in which the water-soluble high-molecular substance contained in said composition B is at least one selected from polyvinyl pyrrolidone, polyethylene oxide, sodium polyacrylate and sodium polymethacrylate.

* * * * *